United States Patent

Christen et al.

[11] Patent Number: 5,232,686
[45] Date of Patent: Aug. 3, 1993

[54] GASTROPROTECTIVE PHARMACEUTICAL PREPARATIONS CONTAINING N-BENZYL-N-((1S,5S)-6,6-DIMETHYLBICYCLO(3,1,1)-HEPT-2-YLETHOXY-ETHYL)-MORPHOLINIUM SALTS

[75] Inventors: Marie-Odile Christen, Paris; Brigitte Noel, Truyes, both of France; Philippi Ilse, Burgwedel, Fed. Rep. of Germany

[73] Assignee: Kali-Chemie Pharma GmbH, Hanover, Fed. Rep. of Germany

[21] Appl. No.: 548,718

[22] Filed: Jul. 6, 1990

[30] Foreign Application Priority Data

Jul. 7, 1989 [DE] Fed. Rep. of Germany ........ 3922387

[51] Int. Cl.$^5$ ............................................. A61K 49/00
[52] U.S. Cl. .................... 424/10; 514/238.8; 514/239.2
[58] Field of Search ............ 514/239.2, 238.8; 424/10

[56] References Cited

U.S. PATENT DOCUMENTS 3,845,048 10/1974 Baronnet ......................... 260/247.7
4,048,313 9/1977 Vincent et al. .................. 424/248.5

FOREIGN PATENT DOCUMENTS 1351505 5/1974 United Kingdom .

OTHER PUBLICATIONS

Bert Rond et al 96CA:974662 1982.
Merck Index 10 ed #7315.
Foussard-Blanpin et al. 108CA:87864e 1988.
Marzio et al. 100CA:203463, 1984.
Droogmans et al., Naumyn-Schmiedeperg's ARch. of Pharmacol. 323:72-77 (1983).
Goodman and Gilman's *The Pharmacological Basis of Terapeutics,* p. 1746.

*Primary Examiner*—Frederick E. Waddell
*Assistant Examiner*—Russell Travers
*Attorney, Agent, or Firm*—Foley & Lardner

[57] ABSTRACT

A method of inhibiting peripheral blood circulation disorders or damage such as hemorrhagic lesions induced by gastrotoxic doses of substances such as alcohol or non-steroid, antiinflammatory medicaments in the gastrointestinal tract of a mammal comprising administering to said mammal an effective peripheral circulation disorder or gastrointestinal damage inhibiting amount of a quaternary N-benzyl-N-{2-[2-((1S,5S)-6,6-dimethylbicyclo[3,1,1]hept-2-yl)-ethoxy]-ethyl}-morpholinium salt, and pharmaceutical compositions comprising a substance having a tendency to induce a peripheral blood circulation disorder or damage such as a hemorrhagic lesion in the stomach and/or intestinal wall of a mammal and an effective peripheral circulation disorder or gastrointestinal damage inhibiting amount of a quaternary N-benzyl-N-{2-[2-((1S,5S)-6,6-dimethylbicyclo[3,1,1]hept-2-yl)-ethoxy]-ethyl}-morpholinium salt.

7 Claims, No Drawings

GASTROPROTECTIVE PHARMACEUTICAL PREPARATIONS CONTAINING N-BENZYL-N-((1S,5S)-6,6-DIMETHYLBICYCLO(3,1,1)-HEPT-2-YLETHOXY-ETHYL)-MORPHOLINIUM SALTS

BACKGROUND OF THE INVENTION

The present invention relates to the use of quaternary N-benzyl-N-{2-[2-((1S,5S)-6,6-dimethylbicyclo[3,1,1-]hept-2-yl)-ethoxy]-ethyl}-morpholinium salts for the prophylaxis and treatment of blood circulation disorders in the peripheral, in particular in the microvascular, region of the stomach or intestinal walls and/or for prophylaxis and treatment of damage to the gastrointestinal tract in larger mammals, particularly in humans, which is caused by gastrotoxic doses of medicaments or chemicals. In particular, the invention relates to the prophylaxis and treatment of damage to the stomach or intestinal tract which may be caused by frequent consumption of nonsteroid antiinflammatory medicines, for instance in rheumatism therapy.

The non-steroid antiphlogistic agents and antirheumatic agents (=non-steroid anti-inflammatory drugs, abbreviated hereinafter as NSAIDs) include, inter alia, substituted benzoic acid derivatives, for instance salicylic acid derivatives such as acetylsalicylic acid (aspirin) or salicylamide; anthranilic acid derivatives such as flufenamic acid; arylacetic acid derivatives, for instance substituted phenylacetic acid derivatives such as Diclofenac or Ibufenac, substituted indole acetic acid derivatives such as indomethacine or substituted 2-phenyl-propionic acid derivatives such as Ibuprofen; quinoline carboxylic acid derivatives; pyrazolindione derivatives, for instance diphenylpyrazolindione derivatives such as phenylbutazone or oxyfenbutazone; phenylpyrazolone derivatives such as phenazone, aminophenazone or propiphenazone; and oxicam derivatives such as piroxicam or tenoxicam.

It is known that NSAIDs have cyclooxygenase-inhibiting effects and thus have an inhibitive effect on endogenous prostaglandin formation. Prostaglandins are found in relatively high concentrations in the walls of the gastrointestinal tract. They play a major role in gastrointestinal physiology and affect a large number of functions in the stomach and intestinal tract. For instance, in addition to inhibiting the secretion of acid, the prostaglandins also enhance the circulation of blood in the stomach mucosa and exhibit mucosa-protective properties.

It is known that, particularly in long-term use, NSAIDs lead to serious damage to the mucosa and walls of the stomach or intestinal tract ranging, for example, from hemorrhages up to very serious stomach bleeding and lesions. $H_2$-receptor-antagonistic substances, which are otherwise successfully used as ulcer therapy agents, cannot effectively prevent NSAID-induced damage to the stomach and intestinal tract.

Quaternary N-benzyl-N-{2-[2-((1S,5S)-6,6-dimethylbicyclo[3,1,1]hept-2-yl)-ethoxy]-ethyl}-morpholinium salts having spasmolytic properties are known from U.S. Pat. No. 3,845,048 (=French Patent No. 2,097,032). Pinaverium bromide (=N-(2-bromo-4,5-dimethoxybenzyl)-N-{2-[2-((1S,5S)6,6-dimethylbicyclo [3,1,1]hept-2-yl)-ethoxy]-ethyl}-morpholinium bromide), for instance, which falls within the scope of the aforementioned patent, is commercially available as a spasmolytic under the trade name "Dicetel TM".

SUMMARY OF THE INVENTION

The object of the present invention is to provide medicaments for prophylaxis and treatment of disorders of the peripheral blood circulation in the stomach and-/or intestinal walls.

A further object of the invention is to provide pharmaceutical compositions particularly suitable for prophylaxis and/or treatment of microvascular circulatory disorders of the stomach and/or intestinal walls.

Another object of the present invention is to develop pharmaceutical preparations for prophylaxis and/or treatment of injuries to the stomach and/or intestinal mucosa induced by gastrotoxic doses of medicaments, in particular NSAIDs, or other chemicals.

These and other objects of the invention are achieved by providing a method of inhibiting peripheral blood circulation disorders in, or damage to, stomach or intestinal walls in a mammal comprising the step of administering to said mammal an effective damage or circulatory disorder inhibiting amount of a quaternary N-benzyl-N-{2-[2-((1S,5S)-6,6-dimethylbicyclo [3,1,1]hept-2-yl)-ethoxy]-ethyl}-morpholinium salt corresponding to the Formula I

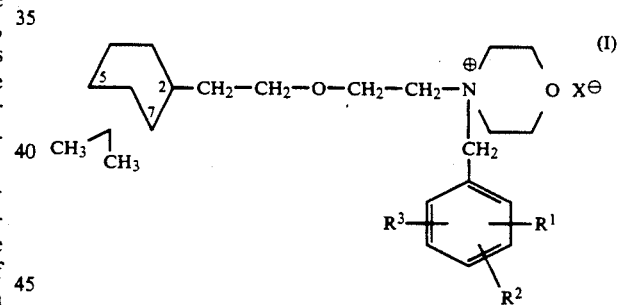

wherein
$R^1$ is hydrogen, halogen, lower alkyl or lower alkoxy,
$R^2$ is hydrogen, halogen, lower alkyl or lower alkoxy,
$R^3$ is hydrogen, halogen, lower alkyl or lower alkoxy, and
$X^-$ represents the anion of a pharmacologically acceptable acid.

According to a preferred aspect of the invention, a method is provided for inhibiting damage to stomach or intestinal walls of a mammal due to consumption of a non-steroid, antiinflammatory medicament, said method comprising the step of administering to said mammal with said non-steroid, antiinflammatory medicament an effective stomach or intestinal wall damage inhibiting amount of a quaternary N-benzyl-N-{2-[2-((1S,5S)-6,6-dimethylbicyclo [3,1,1]-hept-2-yl)-ethoxy]-ethyl}-morpholinium salt corresponding to the formula I

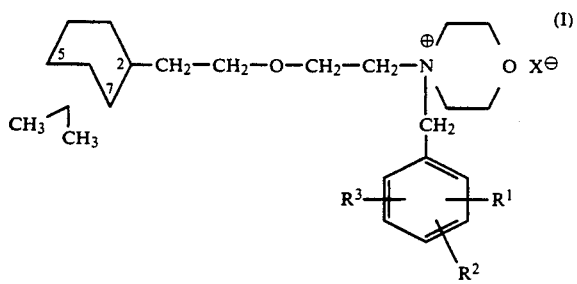

wherein
R¹ is hydrogen, halogen, lower alkyl or lower alkoxy,
R² is hydrogen, halogen, lower alkyl or lower alkoxy,
R³ is hydrogen, halogen, lower alkyl or lower alkoxy, and X⁻ represents the anion of a pharmacologically acceptable acid.

In accordance with yet another aspect of the invention, a method is provided for inhibiting damage to stomach or intestinal walls of a mammal due to consumption of a gastrotoxic substance, said method comprising the step of administering to a mammal which has ingested a toxic dose of a gastrotoxic substance, an effective stomach or intestinal wall damage inhibiting amount of a quaternary N-benzyl-N-{2-[2-((1S,5S)-6,6-dimethylbicyclo [3,1,1]hept-2-yl)-ethoxy]-ethyl}-morpholinium salt corresponding to the formula I

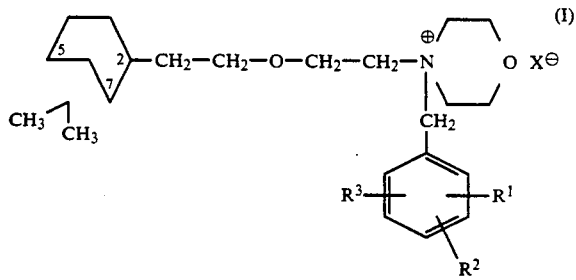

wherein
R¹ is hydrogen, halogen, lower alkyl or lower alkoxy,
R² is hydrogen, halogen, lower alkyl or lower alkoxy,
R³ is hydrogen, halogen, lower alkyl or lower alkoxy, and X⁻ represents the anion of a pharmacologically acceptable acid.

In accordance with a further aspect of the invention a pharmaceutical composition is provided comprising a medicament having a tendency to induce peripheral blood circulation disorders in the stomach or intestinal wall of a mammal or to damage the stomach or intestinal wall of a mammal and an effective peripheral blood circulation disorder or stomach or intestinal wall damage inhibiting amount of a quaternary N-benzyl-N-{2-[2-((1S,5S)-6,6-dimethylbicyclo [3,1,1]hept-2-yl)-ethoxy]-ethyl}-morpholinium salt corresponding to the formula I

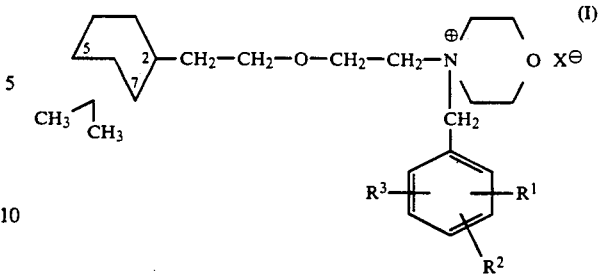

wherein
R¹ is hydrogen, halogen, lower alkyl or lower alkoxy,
R² is hydrogen, halogen, lower alkyl or lower alkoxy,
R³ is hydrogen, halogen, lower alkyl or lower alkoxy, and X⁻ represents the anion of a pharmacologically acceptable acid.

DETAILED DESCRIPTION OF PREFERRED EMBODIMENTS

According to the present invention, quaternary N-benzyl-N-{2-[2((1S,5S)-6,6-dimethylbicyclo [3,1,1]hept-2-yl)-ethoxy]-ethyl}-morpholinium salts of the general Formula I:

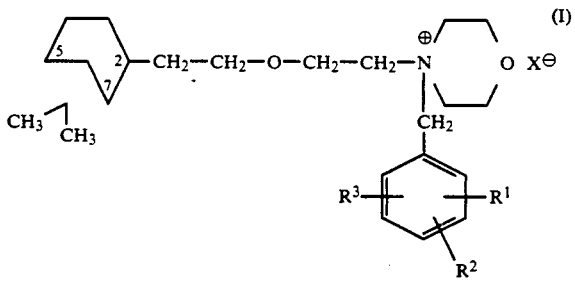

wherein
R¹ is hydrogen, halogen, lower alkyl or lower alkoxy,
R² is hydrogen, halogen, lower alkyl or lower alkoxy,
R³ is hydrogen, halogen, lower alkyl or lower alkoxy, and X⁻ represents the anion of a pharmacologically acceptable acid, are used to produce pharmaceutical preparations for prophylaxis and treatment of blood circulation disorders in the peripheral, in particular microvascular, region of the stomach and intestinal walls and for prophylaxis and/or treatment of damage to the stomach and/or intestinal walls in larger mammals and humans, induced by gastrotoxic doses of medicaments or chemicals, particularly by non-steroid, antiinflammatory medicaments.

In the salts of Formula I, X⁻ represents the anion of a physiologically acceptable inorganic or organic acid. Examples of suitable anions of inorganic acids include halides, particularly bromide and chloride, sulfates and phosphates. Examples of suitable organic acids include lower aliphatic or aromatic sulfonic acids, in particular lower alkyl sulfonic acids such as methane sulfonic acid or benzene sulfonic acids, optionally substituted in the benzene ring by lower alkyl or halogen, such as toluene sulfonic acids.

If in the compounds of Formula I, the substituents R¹ to R³ represent lower alkyl or alkoxy groups, these may be straight-chain or branched and contain from 1 to 4, preferably 1 or 2, carbon atoms, and may in particular represent methyl or methoxy. If the substituents $R^1$ to $R^3$ represent halogen, they may desirably be fluorine, chlorine or bromine. Bromine is particularly preferred. Pinaverium salts such as pinaverium bromide (sold commercially under the name "Dicetel TM") have proved particularly suitable.

The compounds of Formula I are 2-(6,6-dimethylbicyclo[3,1,1]hept-2-yl)-ethanol derivatives, which contain asymmetric centers in positions 1, 2 and 5 of the bicycloheptane ring structure (see Formula I), which centers may each be in the R configuration or in the S configuration. The 2-(6,6-dimethylbicyclo[3,1,1]hept-2-yl)-ethoxy grouping contained in the compounds of Formula I comes from a terpene alcohol which is derived from natural $(-)$-$\beta$-pinene ($=$(1S,5S)-$(-)$-6,6-dimethyl-2-methylenebicyclo[3,1,1]heptane). In this terpene alcohol, the asymmetric centers in the 1 and 5 positions are in the S configuration. Correspondingly, in the 2-[2-((1S,5S)-6,6-dimethylbicyclo[3,1,1]hept-2-yl)ethoxy]-ethanol derivatives of Formula I as well the asymmetric centers in the 1 and 5 positions of the ring structure are in the S configuration, while the asymmetric center in the 2 position may be in the S configuration or R configuration. Thus, the substances of Formula I may occur in two diastereoisomeric forms. Either of the individual stereoisomeric forms of the compounds of Formula I or mixtures thereof may be used in the invention.

The compounds of Formula I fall within the scope of U.S. Pat. No. 3,845,048 and can be prepared in accordance with, or analogously to, the methods described therein. For instance, the compounds of Formula I may be obtained in a known manner by quaternization of compounds of Formula II

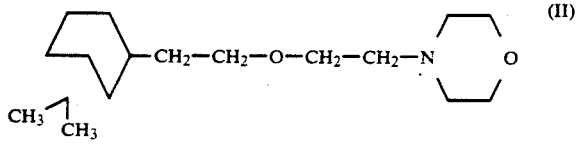

(II)

with benzyl halides of Formula III

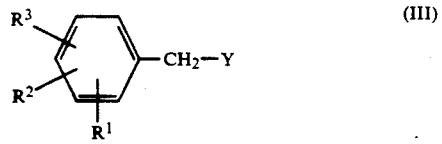

(III)

wherein $R^1$, $R^2$ and $R^3$ have the above meanings, and Y represents halogen.

Compounds of Formula II may be obtained in known manner, for instance in accordance with, or analogously to, the methods described in French Patent No. 2,097,031, starting from the unsaturated terpene alcohol of Formula IV

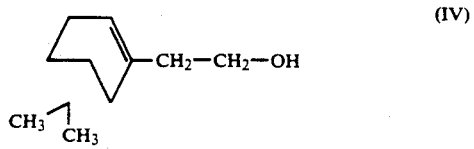

(IV)

by first hydrogenating it to the corresponding saturated alcohol of Formula V

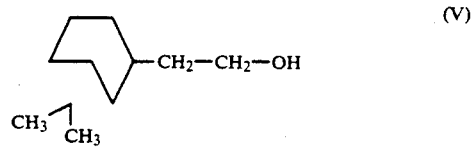

(V)

and then reacting the alcohol of Formula V with a morpholinoethyl halide of Formula VI

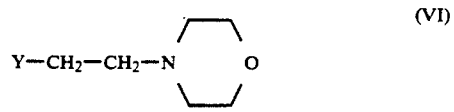

(VI)

wherein Y has the above meaning, or by first reacting the alcohol of Formula IV with the compound of Formula VI and then hydrogenating the reaction product.

In the alcohol of Formula V and its derivatives prepared from natural $(-)$-$\beta$-pinene, the asymmetric centers in positions 1 and 5 of the bicycloheptane structure are in the S configuration, while the asymmetric center in the 2 position may be in the S configuration or R configuration. When the unsaturated alcohol of Formula IV or its reaction product with a compound of formula VI is hydrogenated, a stereoisomer mixture of compounds is produced in which some of the asymmetric centers in the 2 position are in the R configuration and others are in the S configuration. The stereochemical composition of the mixture may vary depending on the type of hydrogenation. If desired, the individual stereoisomeric forms may be concentrated and isolated from the mixtures by conventional separation processes, e.g. fractional crystallization of suitable salts or chromatographic processes. In the further reactions, the configuration of the bicycloheptane structure is retained. Thus, depending on the starting product used, stereoisomer mixtures or stereoisomerically pure substances are obtained as end products of Formula I. Stereoisomer mixtures may be separated in a known manner if desired.

Surprisingly it has been discovered that in addition to their previously known spasmolytic properties, quaternary N-benzyl-N-{2-[2-((1S,5S)-6,6-dimethylbicyclo[3,1,1]hept-2-yl)-ethoxy]-ethyl}-morpholinium salts of Formula I also have the ability to counteract blood circulation disorders in the stomach or intestinal tract, in particular vascular congestion in the peripheral and microvascular region of the stomach or intestinal walls; to counteract the occurrence of stases and hemorrhages, and to exert a protective action in the stomach and intestinal tract against harmful influences of gastrotoxic doses of medicaments or other chemical substances, such as alcohol, which may damage the stomach or intestine walls, in particular those medicaments and substances which exhibit pharmacological activity profiles which include the ability to hinder prostaglandin synthesis. Thus the salts of Formula I have proved effective for prophylaxis and treatment of damage to the stomach or intestine walls caused by NSAIDs, for instance the above-listed antiphlogistic agents and antirheumatic agents.

The protective action of the compounds of Formula I against hemorrhages and NSAIDs-induced hemorrhagic lesions in the stomach or intestinal tract can be demonstrated by standard pharmacological tests on animals and in clinical studies.

Description of the Pharmacological Tests

1. Determination of the inhibiting effect of the compounds on Aspirin induced Lesions.

Groups of at least 6 male rats having a body weight of 180–200 grams were used per test dose. The animals were kept without food for 24 hours, with unlimited supplies of water being available. The test substances were administered per os suspended in 0.5 ml suspension medium (1% methylcellulose solution) per 100 g animal weight. A control group of animals was given only the corresponding volume of suspension medium. One hour after administration of the test substances, the animals were administered per os 200 mg/kg acetylsalicylic acid likewise suspended in 0.5 ml suspension medium per 100 g animal weight. The animals were sacrificed 5 hours after the administration of aspirin. The stomachs were removed and opened, and the number and size of the mucosal lesions were assessed. They were evaluated in modified manner according to O. Muenchoff (Arzneim. Forsch. (Drug Res.) 4, 341–344 (1954)). Mean values and standard deviations were calculated, and the inhibiting effect of the test substances in % was determined compared with the control group.

The results are reproduced in the following Table I.

TABLE I

| Active Substance | Dose in $\mu$mol/kg p.o. | Inhibition of Aspirin induced lesions in rat stomachs % inhibition |
|---|---|---|
| Pinaverium bromide[1] | 100 | 53 |
|  | 215 | 88 |
| trans-pinaverium bromide[2] | 100 | 61 |
|  | 215 | 67 |
| cis-pinaverium bromide[3] | 100 | 27 |
|  | 215 | 70 |

[1]Stereoisomer mixture
[2]Substituent in 2 position is trans to dimethylmethylene group.
[3]Substituent in 2 position is cis to dimethylmethylene group.

2. Evaluation of protective activity of test substances against vascular damage (hemorrhagic lesions) induced by harmful substances in rat gastrointestinal tracts.

For the tests, groups of 3 or 4 Sprague-Dawley rats in each case, having a body weight of 160–200 g, were used per test dose and as a group of control animals. The tests were repeated twice and the results were averaged. The rats which had been kept without food were administered a suspension of the test dose in a solution of cooking salt, or as a control only the suspension agent, intragastrically by means of a stomach tube. After a period of 5 or 30 minutes or 1, 2 or 6 hours respectively, 1 ml of the harmful agent (100% ethyl alcohol, 0.6 n aqueous hydrochloric acid solution or 0.2 n aqueous sodium hydroxide solution) was administered intragastrically to each of the animals. One hour after administration of the harmful agent, the animals were sacrificed. During the autopsy, the extent of the lesions occurring in the stomach/intestine walls was assessed and the surface areas of the lesions were measured by computerized planimetry and calculated as a percentage of the glandular stomach surface.

The test results obtained with pinaverium bromide are reproduced in the following Table II.

TABLE II

| Pretreatment with Pinaverium Bromide | | | Damage |
|---|---|---|---|
| Dose mg/100 g Rat i.g. | Time Interval | Harmful Agent 1 ml | Hemorrhagic Lesions % of the glandular Stomach Surface |
| 0 | 30 min | $C_2H_5OH$ | 21.6 ± 1.7 |
| 10 | 30 min | $C_2H_5OH$ | 0 |
| 10 | 1 hour | $C_2H_5OH$ | 0 |
| 10 | 2 hours | $C_2H_5OH$ | 0.1 ± 0.1 |
| 0 | 30 min | 0.6 n HCl | 17.6 ± 2.7 |
| 10 | 30 min | 0.6 n HCl | 0.7 ± 0.6 |
| 0 | 30 min | 0.2 n NaOH | 22.9 ± 1.9 |
| 10 | 30 min | 0.2 n NaOH | 0.3 ± 0.2 |

The foregoing pharmacological test results show that after oral administration the substances develop a strong protective action against the harmful influence of a large number of chemical substances in the gastrointestinal tract, an action which is both quick to begin and long-lasting, and that they can effectively inhibit the occurrence of hemorrhagic erosion.

The active substances used in the invention are distinguished by a combination of spasmolytic properties with cytoprotective effects in the stomach or intestinal tract, in particular in the microvascular region of the stomach and intestine walls, and are capable of protecting the stomach and intestinal tract from hemorrhagic damage induced by gastrotoxic doses of medicaments, in particular NSAIDs, and other chemical substances.

The substances may be used according to the invention as active substances for the production of pharmacological preparations for the prophylaxis and treatment of blood circulation disorders in the peripheral, in particular microvascular, region of the stomach and/or intestine walls and for prophylaxis and treatment of damage to the stomach/intestine walls induced by gastrotoxic doses of medicaments, in particular NSAIDs, or chemicals. The doses to be used may differ individually, and will naturally vary according to the type of condition to be treated and the substance used. Generally speaking, however, medicaments having an active substance content of from about 10 to about 100 mg, in particular from about 20 to about 60 mg, of active substance per individual dose are suitable for oral administration to humans and other large mammals.

The compounds may be contained according to the invention, together with conventional pharmaceutical adjuvants and/or carriers, in solid or liquid pharmaceutical preparations. Examples of solid orally administrable preparations include tablets, capsules, granules or dragees. These preparations may contain conventional pharmaceutical inorganic and/or organic carriers, e.g. talcum, lactose or starch, as well as conventional pharmaceutical adjuvants, for instance lubricants or tablet disintegrating agents. Advantageously the preparations are provided with a taste-concealing coating. Liquid preparations such as suspensions or emulsions of the active substances, preferably in microencapsulated form, may contain conventional diluents such as water or oils and/or suspension agents such as polyethylene glycols and the like. Other adjuvants may also be added, such as preservatives, taste improvers and the like.

The active substances may be mixed with the pharmaceutical adjuvants and/or carriers and formulated in known manner. For the production of solid medicament forms, the active substances may for instance be mixed in conventional manner with the adjuvants and/or carriers and may be granulated in the wet or dry state. Depending on the type of additives used, optionally a powder which can be made directly into tablets can also be obtained by simple mixing. The granules or powder may be poured directly into capsules or be pressed into tablet cores in a conventional manner. These may then be made into dragees in a known manner, if desired.

According to the invention, the substances are especially used for the prophylaxis and the treatment of gastrointestinal hemorrhages which are caused by taking NSAIDs and which may lead to life-threatening stomach bleeding, in particular in those patients who take fairly large quantities of NSAIDs over a fairly long time, for instance within the framework of rheumatism therapy. Accordingly, it has proved advantageous in accordance with the invention to carry out co-medication with a compounds of Formula I, in particular pinaverium bromide, in cases of therapy with NSAIDs over longer periods of time. By means of combined use of an NSAID with a compound of Formula I, in particular pinaverium bromide, the harmful side-effects of the NSAID on the gastrointestinal tract, in particular the effects causing stomach bleeding, can be suppressed and the compatibility of NSAID therapy can be substantially improved. The ratio of the amount of the active substance selected from the group of NSAIDs to the amount of the compound of Formula I may vary depending on the type of NSAID used, and may for instance lie between 2:1 and 1:10, preferably 1:1 and 1:3, parts by weight. The active substances may be administered separately in separate pharmaceutical preparations, or may be formulated together in one pharmaceutical preparation.

The following examples are intended to illustrate the invention in further detail without, however, limiting its scope.

EXAMPLE 1

Pinaverium-Containing Tablets (pinaverium bromide)

Ingredients:
50 parts pinaverium bromide
80 parts microcrystalline cellulose
17 parts corn starch
18 parts lactose
1 part hydrophobic silicon dioxide
3 parts talcum
1.5 parts magnesium stearate Pinaverium bromide was mixed with cellulose, corn starch, lactose and silicon dioxide. Then talcum and magnesium stearate were mixed with this mixture. The resulting admixture was pressed into 170 mg tablets.

EXAMPLE 2

Pinaverium Bromide Film Tablets

Ingredients:
50 parts pinaverium bromide
80 parts microcrystalline cellulose
17 parts corn starch
18 parts lactose
1 part hydrophobic silicon dioxide
8 parts talcum
1.5 parts magnesium stearate
4.5 parts acrylic resin
1 part polyethylene glycol Pinaverium bromide was mixed with cellulose, corn starch, lactose and silicon dioxide. Then talcum and magnesium stearate were mixed with this mixture. The resulting admixture was pressed into 175 mg tablets. The tablets were subsequently provided with a film coating which was soluble in gastric juices and consisted of acrylic resin, polyethylene glycol and talcum.

EXAMPLE 3

Pinaverium Bromide Tablets

Ingredients:
50 parts pinaverium bromide
80 parts microcrystalline cellulose
17 parts corn starch
18 parts lactose
1 part hydrophobic silicon dioxide
3 parts talcum
1.5 parts magnesium stearate Pinaverium bromide was mixed with cellulose, lactose and 12 parts of the corn starch. The mixture was worked into a paste formed of 5 parts corn starch and 45 parts water, and the resulting granules were dried. After sieving the dried granules, talcum, silicon dioxide and magnesium stearate were added, and the resulting mixture was pressed into 250 mg tablets.

EXAMPLE 4

M Pinaverium Bromide Film Tablets

Ingredients:
50 parts pinaverium bromide
80 parts microcrystalline cellulose
17 parts corn starch
18 parts lactose
1 part hydrophobic silicon dioxide
3 parts talcum
1.5 parts magnesium stearate
3 parts hydroxypropylmethylcellulose
1 part polyethylene glycol Pinaverium bromide was mixed with cellulose, lactose and 12 parts of the corn starch. The mixture was worked into a paste formed of 5 parts corn starch and 45 parts water, and the resulting granules were dried. After sieving the dried granules, talcum, silicon dioxide and magnesium stearate were added, and the resulting mixture was pressed into 170 mg tablets.

The tablets were provided with a film coating which consisted of hydroxypropylmethylcellulose and polyethylene glycol and was soluble in gastric juices.

EXAMPLE 5

Pinaverium Bromide Capsules

Ingredients:
50 parts pinaverium bromide
80 parts microcrystalline cellulose
17 parts corn starch
18 parts lactose
1 part hydrophobic silicon dioxide
3 parts talcum
1 5 parts magnesium stearate Pinaverium bromide was mixed with cellulose, lactose and 12 parts of the corn starch. The mixture was worked into a paste formed of 5 parts corn starch and 45 parts water, and the resulting granules were dried. After sieving the dried granules, talcum, silicon dioxide and magnesium stearate were added, and the resulting mixture was filled into hard gelatine capsules of a desired size.

If desired, the granules may also be poured into sachets in portions corresponding to the desired individual dose.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all modifications falling within the ambit of the appended claims and equivalents thereof.

What is claimed is:

1. A method of treating chronic damage to the mucosa and walls of the stomach selected from the group of mucosal and microvascular injuries and microvascular blood circulation disorders in the peripheral microvascular region of stomach walls in a mammal caused by long-term consumption by said mammal of a non-steroid antiinflammatory drug having a tendency upon prolonged administration to induce damage to the mucosa and walls of the stomach, said method comprising the step of administering to said mammal an effective gastrointestinal damage treating amount of a quaternary N-benzyl-N-(2-[2-(1S,5S)-6,6-dimethylbicyclo-[3,1,1]hept-2-yl-ethoxy]ethyl)-morpholinium salt corresponding to the Formula I

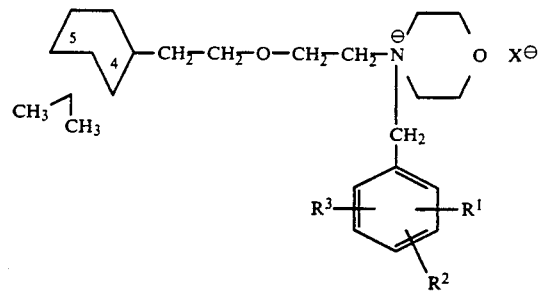

wherein
R¹ is hydrogen, halogen, lower alkyl or lower alkoxy,
R² is hydrogen, halogen, lower alkyl or lower alkoxy,
R³ is hydrogen, halogen, lower alkyl or lower alkoxy, and
X represents the anion of a pharmacologically acceptable acid.

2. A method according to claim 1, wherein said compound of Formula I is administered to a mammal consuming gastrotoxic doses of a non-steroid antiinflammatory medicament together with said non-steroid antiinflammatory medicament.

3. A method according to claim 2, wherein said antiinflammatory non-steroid drug and said compound of Formula I are administered in a weight ratio of antiinflammatory non-steroid drug to compound of Formula I of from 2:1 to 1:10.

4. A method according to claim 1, wherein X represents an anion of a pharmacologically acceptable acid selected from the group consisting of hydrohalic acids, lower aliphatic sulfonic acids and aromatic sulfonic acids.

5. A method according to claim 1, wherein said salt is a N-(2-bromo-4,5-dimethoxybenzyl)-N-(2-[2-((1S,5S)-6,6-dimethylbicyclo [3,1,1]hept-2-yl)-ethoxy]-ethyl)-morpholinium salt of a pharmacologically acceptable acid.

6. A method according to claim 5, wherein said salt is a salt of a pharmacologically acceptable acid selected from the group consisting of hydrohalic acids, lower aliphatic sulfonic acids and aromatic sulfonic acids.

7. A method according to claim 6, wherein said salt is a bromide salt.

* * * * *